United States Patent [19]
Peyton et al.

[11] Patent Number: 5,641,642
[45] Date of Patent: Jun. 24, 1997

[54] IN SITU BIOFILM COUPON DEVICE

[75] Inventors: Brent M. Peyton, Kennewick; Michael J. Truex, Richland, both of Wash.

[73] Assignee: Battelle Memorial Institute, Richland, Wash.

[21] Appl. No.: 534,142

[22] Filed: Sep. 26, 1995

[51] Int. Cl.$^6$ .............................. C12Q 1/64; C12M 3/00; G01N 33/24
[52] U.S. Cl. .............................. 435/9; 435/30; 435/308.1; 435/309.1; 436/28; 436/30; 73/863.21; 73/152.25; 73/152.26
[58] Field of Search .............................. 435/9, 30, 308.1, 435/309.1; 436/28, 30; 73/61.41, 61.59, 863.23, 863.81, 863.82, 863.21, 152.25, 152.26

[56] References Cited

U.S. PATENT DOCUMENTS

| | | | |
|---|---|---|---|
| 1,133,218 | 3/1915 | Beecher | 73/152.23 |
| 4,745,801 | 5/1988 | Luzier | 73/155 |
| 4,857,473 | 8/1989 | Magaritz et al. | 436/177 |
| 5,235,863 | 8/1993 | Bailey et al. | 73/863.23 |

*Primary Examiner*—David A. Redding
*Attorney, Agent, or Firm*—Stephen R. May

[57] ABSTRACT

An apparatus for characterization of in-situ microbial biofilm populations in subsurface groundwater. The device permits biofilm-forming microorganisms to adhere to packing material while emplaced in a groundwater strata, so that the packing material can be later analyzed for quantity and type of microorganisms, growth rate, and nutrient requirements.

6 Claims, 1 Drawing Sheet

IN SITU BIOFILM COUPON DEVICE

This invention was made with Government support under Contract DE-AC06-76RLO 1830 awarded by the U.S. Department of Energy. The Government has certain rights in the invention.

FIELD OF THE INVENTION

The present invention relates to subsurface sampling devices, and more particularly to an in-situ biofilm coupon for enabling growth on and subsequent analysis of subsurface in-situ microorganisms.

BACKGROUND OF THE INVENTION

Through a number of different methods, the groundwater has been contaminated in many areas with a variety of noxious chemicals. While there are chemical methods available to remediate such pollution, a technique known as "in-situ bio-remediation" may be preferred in many cases. For example, if a population of microbial organisms capable of remediating a particular chemical pollutant either already exists in situ, or can be introduced to the subsurface zone requiring remediation, introducing excess nutrients to the microbial population to stimulate growth and biological activity can greatly enhance bio-remediation. However, before such bio-remediation can occur, a census of microbial growth must be accurately known in order to provide optimal nutrients for growth of the desired organisms.

Previously, microbial characterization typically occurred by sampling groundwater collected in a sampling well or tube at the desired location. However, it has been shown that the number of microorganisms collected free-floating in a water sample bears little or no relationship to the size of the population adhered to the subsurface strata—it is invariably smaller by a significant amount. Therefore, wells have been drilled so that soil cores can be taken, and the microorganisms therein analyzed. This method is expensive and is limited by the number of wells that can be drilled at a given location.

In groundwater, virtually all of the microbial activity is associated with biofilms—aggregations of microorganisms attached to structures as opposed to free-floating. For example, if the water collected in wells is used, it is estimated that approximately 100 liters of groundwater must be filtered to provide the same biomass that might be available from an equivalent volume of a single core sample.

The use of in-situ coupons is contrary to standard bioremediation monitoring methods that are directed at free-floating microorganisms. Current methods for the use of RNA probes require that over 500 liters of contaminated groundwater be pumped to the surface to recover approximately 0.5 grams of biomass for analysis. As a result, the 500 liters of groundwater, per sample, must be disposed of as hazardous waste. Additionally, the microorganisms that are recovered represent only the population in the ground water, not the quantity actually in the strata that are responsible for the bulk of the bioremediation.

In addition, there is a need for a system to measure the accumulation rate of the in-situ biofilm formation during the active bioremediation process, and to determine the effects of in-situ biomass transport processes such as cellular attachment and detachment.

SUMMARY OF THE INVENTION

The present invention is a method and apparatus for accurately measuring the population and growth rate of in-situ biofilm-forming microorganisms in subsurface groundwater strata. The apparatus comprises a sampling tube extending downwardly to a subsurface zone to be measured, the tube having a perforated portion therein to permit the flow of ground water therein. The sampling tube may be removably suspended within a permanent larger-diameter outer tube. The sampling coupon comprises a porous exterior wall in fluid communication through the sampling tube to the groundwater. The sampling coupon is packed with a packing material, such as glass fibers, glass beads or aquifer sediments upon which the biofilm microorganisms are permitted to grow. The sampling coupon is provided with end caps on either end, preferably provided with, for example, O-rings, for securely segregating the sampling coupon within the sampling tube from adjacent areas of the sampling tube. Finally, the sampling coupon is provided with means, such as hook-and-eyelets on the end caps to enable a plurality of such sampling coupons to be utilized at once.

DETAILED DESCRIPTION OF THE INVENTION

Figure 1:
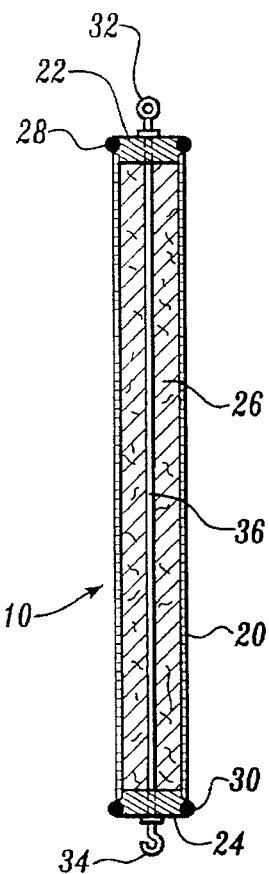
FIG. 1 illustrates a longitudinal sectional view of the bioremediation coupon of the present invention.

As illustrated in FIG. 1, the sampling coupon 10 comprises a porous exterior wall 20, a pair of end caps 22 and 24, and a packing material 26 constrained within the wall 20. The end caps 22 and 24 are provided with sealing means 28 and 30, and means 32 and 34, to affix a plurality of the coupons 10 one to the other. In order to provide rigidity to the apparatus, a steel rod, or bolt, 36, may be provided to interconnect the end caps 22 and 24. While the packing material 26 is illustrated as taking up relatively all the space within the exterior wall, such as with glass fibers, it in fact may exist in any form, such as glass beads or sand.

Figure 2:
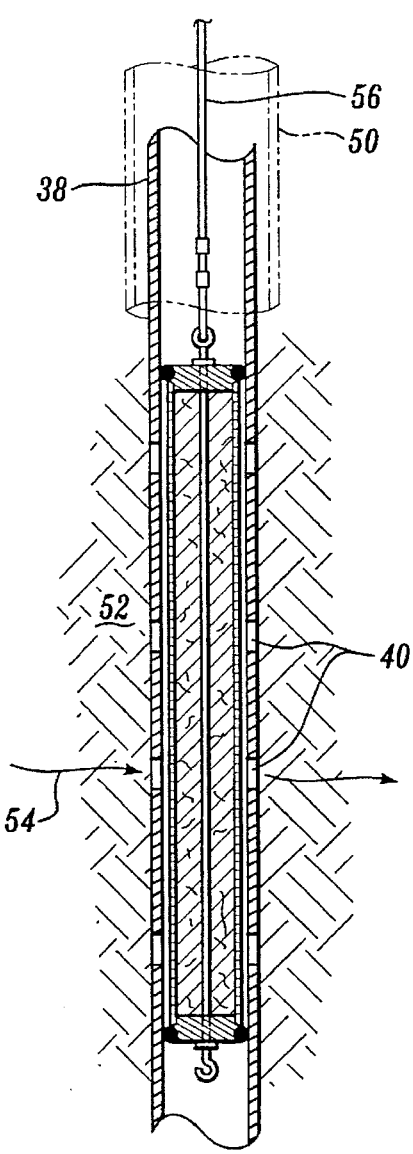
FIG. 2 illustrates the bioremediation coupon of the present invention deployed in a subsurface environment.

FIG. 2 illustrates the sampling coupon 10 deployed in a subsurface configuration. A sampling tube 38 is provided with a perforated portion 40. If necessary or desirable, the sampling tube 38 may be deployed within a permanent, larger diameter outer tube 50. In either case, the sampling tube 38 is positioned in-situ in a strata 52 within the groundwater 54 zone.

Figure 3:
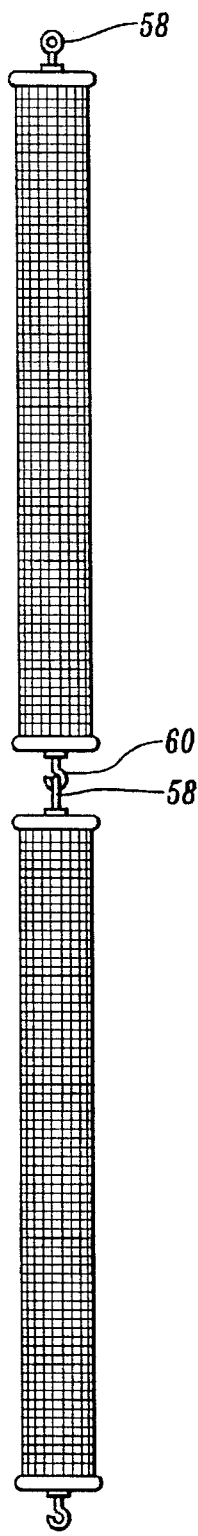
FIG. 3 illustrates a plurality of the bioremediation coupons of the present invention affixed to one another.

In operation, the sampling coupon 10 is located adjacent the perforated portion 40 of the sampling tube 38, so that the groundwater containing the biofilm-forming microorganisms in the groundwater can flow through the sampling tube 38 and the sampling coupon 10. The sampling coupon 10 is lowered and raised by a cable 56 affixed to an attachment means 58. As illustrated in FIG. 3, multiple coupons 10 can be affixed to one another by additional cooperating attachment means 60.

The porous exterior wall 20 may be any material sufficient to hold the packing material in place while permitting groundwater 54 to flow therethrough. It has been found that a rigid screen constructed of stainless steel is preferable, constructed as a cylinder and packed with glass wool, although any durable material will suffice. The packing material is used to increase the surface area for biomass attachment and to facilitate biofilm analysis. Therefore, almost any material that promotes microorganism growth, withstands the rigors of placement down-hole, and permits biomass analysis when retrieved, may be used. Applicant has found that glass fibers or glass beads work well.

The use of a permanent outer tube 50 permits reuse of the perforated sampling tube 38 and lower cost over time. The sampling coupon 10 may preferably be emplaced within the sampling tube 38 such that the sealing means 28, 30 seal off the sampling tube 38 on either side of the perforations 40, thereby assuring integrity of samples taken. The coupon 10 may be lowered into place and left for a period of time sufficient to enable adequate biofilm-forming organisms to grow on the packing material 26 in large enough quantities to make accurate measurements of population size and growth rate.

Many analyses may be performed on the packing material upon retrieval, including identity of microorganisms, quantity of biomass, physiological state of biomass, total attached solids, volatile attached solids, most probable concentration, microbial plate counts, protein concentration, nutrient requirements, growth rate, and the like.

EXAMPLE

PROCEDURE: Glass wool having approximately 10 um diameter strands was firmly packed into a 7" cylindrical sampling coupon constructed of 304 stainless steel, with 12 grids/inch. The total glass wool weight was 1.15 g and the total volume available within the sampling coupon was 12.6 mL, yielding a packed density of 0.091 g/mL. The packed coupon was autoclaved and placed in sampling wells for 12 and 22 days. Total and denitrifying viable cells were enumerated using both denitrifying MPN broth and PTYG plate counts. The remaining portion of the glass wool was frozen for molecular probe analysis.

RESULTS: Biomass concentrations of $10^7$ to $10^8$ colony forming units (CFU) per gram of glass wool were obtained. A numerical biofilm model was used to fit the observed data and to compare the effects of the different growth rates on the predicted accumulation of biomass. With the numerical curve fit, it was observed that the growth rate had little effect on the total amount of biofilm accumulation on the coupon. It is believed that to obtain the amount of biomass developed by the present invention from the liquid phase, it would be necessary to filter cells from about 10–100 L of groundwater.

While the invention has been particularly described with reference to the description and drawings, the scope of this invention should be limited only by the issued claims. Embodiments reasonably falling within the scope of this description should be considered within the scope of this invention.

We claim:
1. Apparatus for characterizing in situ microbial biofilm populations in subsurface groundwater and for accumulating biofilm for subsequent analysis, comprising:
   (a) a sampling tube extending downwardly at least to a groundwater location to be analyzed, and having a perforated portion therein;
   (b) a sampling coupon having
      (i) a porous exterior wall in fluid communication with said groundwater;
      (ii) end caps enclosing each end of the exterior wall and having sealing means thereon to seal the end cap against an inner surface of the sampling tube;
      (iii) packing material within the porous exterior wall adapted to capture biofilm-forming biomass in the groundwater;
   (c) means to lower the sampling coupon to the perforated portion of the sampling tube such that the porous exterior wall of the sampling coupon is adjacent the perforated portion of the sampling tube.

2. The apparatus of claim 1, wherein the end caps are provided with attachment means to enable multiple sampling coupons to be removably affixed one above the other when lowered into the sampling tube.

3. The apparatus of claim 1, wherein the sealing means comprise O-rings disposed about the periphery of the end cap.

4. The apparatus of claim 1, wherein the packing material comprises glass wool.

5. The apparatus of claim 1, wherein the packing material comprises glass beads.

6. Method for sampling and measuring biofilm-forming microbial biomass in subsurface groundwater, comprising the steps of:
   (a) placing a sampling tube having a perforated section located at a groundwater location to be analyzed into subsurface strata;
   (b) permitting groundwater to flow into the perforated section of the sampling tube;
   (c) lowering a bioaccumulating coupon having a biofilm-collecting material therein to the perforated section;
   (d) sealing the sampling tube from the groundwater above and below the perforated section with the coupon in place in fluid communication with the groundwater;
   (e) leaving the coupon in place for a period of time sufficient to permit biofilm-forming microbial biomass to accumulate on the biofilm-collecting material.

\* \* \* \* \*